United States Patent
Becker et al.

(10) Patent No.: US 6,294,707 B1
(45) Date of Patent: *Sep. 25, 2001

(54) FLUIDIZED BED REACTOR AND PROCESS FOR PRODUCING 5-ETHYLIDENE-2-NORBORNENE

(75) Inventors: Christopher Lynn Becker, Baton Rouge, LA (US); James Richardson Lattner, Seabrook, TX (US); Mark T. Swihart, Minneapolis, MN (US)

(73) Assignee: ExxonMobil Chemical Patents Inc., Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/920,486

(22) Filed: Aug. 29, 1997

Related U.S. Application Data

(60) Provisional application No. 60/024,891, filed on Sep. 30, 1996.

(51) Int. Cl.[7] .............................. C07C 5/23; C07C 5/25; C07C 5/22
(52) U.S. Cl. .................. 585/377; 585/363; 585/664; 585/671; 585/921; 585/924; 585/925
(58) Field of Search .................. 208/157; 585/921, 585/924, 925, 664, 671, 363, 377

(56) References Cited

U.S. PATENT DOCUMENTS

| | | | |
|---|---|---|---|
| 2,767,128 | 10/1956 | Burtis | 196/52 |
| 2,987,465 | * 6/1961 | Johanson | 208/408 |
| 3,788,973 | * 1/1974 | Wolk et al. | 208/157 |
| 3,826,739 | * 7/1974 | Kubo et al. | 208/157 |
| 3,901,660 | 8/1975 | Ohorodnik et al. | 23/288 |
| 3,932,269 | * 1/1976 | Lehman | 208/157 |
| 4,108,682 | * 8/1978 | Takeda et al. | 134/25.1 |
| 4,720,601 | * 1/1988 | Suzukamo et al. | 585/377 |
| 4,857,496 | 8/1989 | Lopez et al. | 502/220 |

FOREIGN PATENT DOCUMENTS

| | | |
|---|---|---|
| 1 169 924 | 1/1959 | (FR). |
| 1 438 566 | 6/1976 | (GB). |
| 2 094 810 | 9/1982 | (GB). |
| WO 95 13136 | 5/1995 | (WO). |

OTHER PUBLICATIONS

Bartholomew, C., et al., "Keeping the Catalyst in Mind from the Beginning," *Chemical Engineering*, pp. 70–75, Jun. 1994.

Papa, G., et al., "Correlating Throughout and Backmixing in Fluidized Beds," *Hydrocarbon Processing*, pp. 81–87, Jan. 1995.

Liang, W. G., "Effect of Radial Flow Nonuniformity on the Alkylation Reaction in a Liquid–Solid Circulating Fluidized Bed (LSCFB) Reactor," *Ind. Eng. Chem. Res.* vol. 36, pp. 4651–4657, 1997.

PCT International Search Report (International application No. PCT/US97/15256).

* cited by examiner

Primary Examiner—Walter D. Griffin

(57) ABSTRACT

The present invention is directed to a continuous process for producing a desired hydrocarbon product using a heterogeneous slurry catalyst, to the product of said process, and to the reactor utilized in such process.

12 Claims, 3 Drawing Sheets

FLUIDIZED BED REACTOR AND PROCESS FOR PRODUCING 5-ETHYLIDENE-2-NORBORNENE

This application claims priority to U.S. Provisional Patent Application No. 60/024,891, filed Aug. 30, 1996.

FIELD OF THE INVENTION

The present invention relates to a method for carrying out a chemical reaction with at least one reactant in the liquid phase using a solid catalyst. In particular, the present invention relates to a continuous method for processing liquid hydrocarbon reactants using a heterogeneous catalyst. Specifically, the present invention relates to a continuous method for processing liquid hydrocarbon reactants using a solid catalyst in powder form to achieve high conversions.

BACKGROUND OF THE INVENTION

Catalytic reactions involving at least one or more liquid reactants with a solid catalyst are common. Typically, such reactions are carried out in one of several different types of reactors.

As taught in Kirk-Othmer, Volume 19, 1983 edition, pages 880–891, which is incorporated by reference herein, many reactors, configurations, and designs have evolved over the years. The specific reactor selection is based on the physical properties of each of the feeds to the reactor and to each of the products from the reactor, i.e. vapor, liquid, solid, or combinations; the characteristics of the chemical reactions to be carried out in the reactor, i.e. reactant concentrations, reaction rates, operating conditions, and heat addition or removal; the nature of any catalyst used, i.e. activity, life, and physical form; and the requirements for contacting reactants and removing products, i.e. flow characteristics, transport phenomena, and mixing and separating mechanisms. These factors are interdependent and must be considered together. The requirements for contacting reactants and removing products are the paramount focus of reactor technology, with the other factors usually being set by the selection of the reacting system and intended levels of reactant conversion and product selectivity.

Processes considered "high conversion" are those in which the chemical reaction approaches the point of equilibrium. One example of such a process is the isomerization of 5-vinyl-2-norbornene ("VNB") to 5-ethylidene-2-norbornene ("ENB"). ENB is used as a termonomer in the production of films for food wrap. When producing ENB, greater than 99.7% conversion is required in order to meet governmental health regulations.

Typical liquid phase reactions with solid catalysts that require high conversions (conversions approaching equilibrium) include a batch reaction with slurry catalyst, a continuous reaction in a fixed static bed reactor, or a series of continuous stirred or mixed reactors with slurry catalysts.

Fluid bed reactors, in which at least one of the reactions occurs in the gas phase, or in the liquid phase with a gas phase also present, offer the following advantages of (1) small catalyst particles can be utilized, which offer excellent mass transfer to the catalytic surface, but which are too small to practically use in a fixed bed due to high pressure drops; (2) high coefficients of heat transfer, which allow for the continuous addition or removal of heat for excellent temperature control of the reaction; and (3) catalysts can be easily added and withdrawn, either continuously or periodically, which is useful when a catalyst is used that loses activity over time and must be purged.

For example, U.S. Pat. No. 3,901,660 teaches a method to provide mixing of a heterogeneous catalyst in a fluidized bed reactor by introducing bubbles to mix the reactant together. The gas may be inert and be used simply to agitate the bed or may be non-inert and act also as a reactant.

However, such fluidized beds, which have a gas phase present, are not useful for high conversion reactions in which a close approach to equilibrium is desired, because the agitation achieved by the gas bubbles results in back-mixing of the liquid; thus, creating a mixed flow regime. Thus, the close approach to equilibrium is prevented.

Other examples of liquid phase reactions using a solid catalyst employ either mixed slurry reactors, fixed beds, or fluid beds with a gas phase also present. In all of these examples, high conversions are achieved by placing multiple mixed reactors in series, or by batch reactions, or by use of fixed bed reactors, or by use of co-current liquid/catalyst flow reactors.

There are several ways to achieve high conversion reactions, including batch reactor, a plug flow reactor, or several continuous stirred tanks. In industry, it is most pragmatic to use several continuous stirred tanks and try to put as many continuous stirred tanks to achieve plug flow as if one was using a fixed bed. When one uses a fixed bed though, one needs a solid catalyst. However, if one has a catalyst requirement that it be in a powder form, a fluidized bed is required, which therefore results in a loss of conversion rates.

It would be desirable if a process method could be developed to enable one to carry out a chemical reaction between liquid reactants using a powdered catalyst in a continuous mode of operation, without having to sacrifice conversion rates, rather than having to operate in a batch system.

SUMMARY OF THE INVENTION

The present invention relates to a continuous process for producing a desired hydrocarbon product from a conversion chemical reaction which utilizes a solid catalyst in powdered form comprising:
  a) providing a reactor having a top portion and a bottom portion wherein the length to diameter ratio of the reactor is greater than about 2:1;
  b) loading a powdered heterogeneous catalyst into said reactor;
  c) feeding to said bottom portion of said reactor at least one liquid reactant at a velocity sufficient to disperse said catalyst in said liquid reactant without the use of agitation or back mixing to form a bed reaction zone wherein said velocity is at least equal to the minimum fluidization velocity and less than the minimum entrainment velocity wherein catalyst exits said bed reaction zone in the liquid;
  e) subjecting said liquid reactant to catalyzing conditions in said bed reaction zone whereby said desired hydrocarbon product is formed; and
  f) removing said desired hydrocarbon product from said top portion of said reactor.

Another embodiment relates to a hydrocarbon product produced by a process using a heterogeneous slurry catalyst comprising
  a) providing a reactor having a top portion and a bottom portion;
  b) feeding to said reactor a slurry comprising a powdered heterogeneous catalyst;

c) subsequently feeding to said bottom portion of said reactor at least one liquid reactant at a velocity sufficient to disperse said catalyst in said liquid reactant to form a dense slurry bed reaction zone having a top portion and a bottom portion;

d) subjecting said liquid reactant to appropriate catalyzing conditions whereby said desired product is formed; and e) removing said desired product from said top portion of said reactor.

An additional embodiment includes a reactor for producing a desired hydrocarbon product using a heterogeneous slurry catalyst comprising a) a top portion and a bottom portion;

b) means for feeding a slurry to said reactor comprising a powdered heterogeneous catalyst;

c) means for subsequently feeding to said bottom portion of said reactor at least one liquid reactant at a velocity sufficient to disperse said catalyst in said reactor to form a dense slurry bed reaction zone having a top portion and a bottom portion;

d) means for subjecting said liquid reactant to appropriate catalyzing conditions whereby said desired product is formed; and e) means for removing said desired product from said top portion of said reactor.

DETAILED DESCRIPTION OF THE INVENTION

Figure 1:
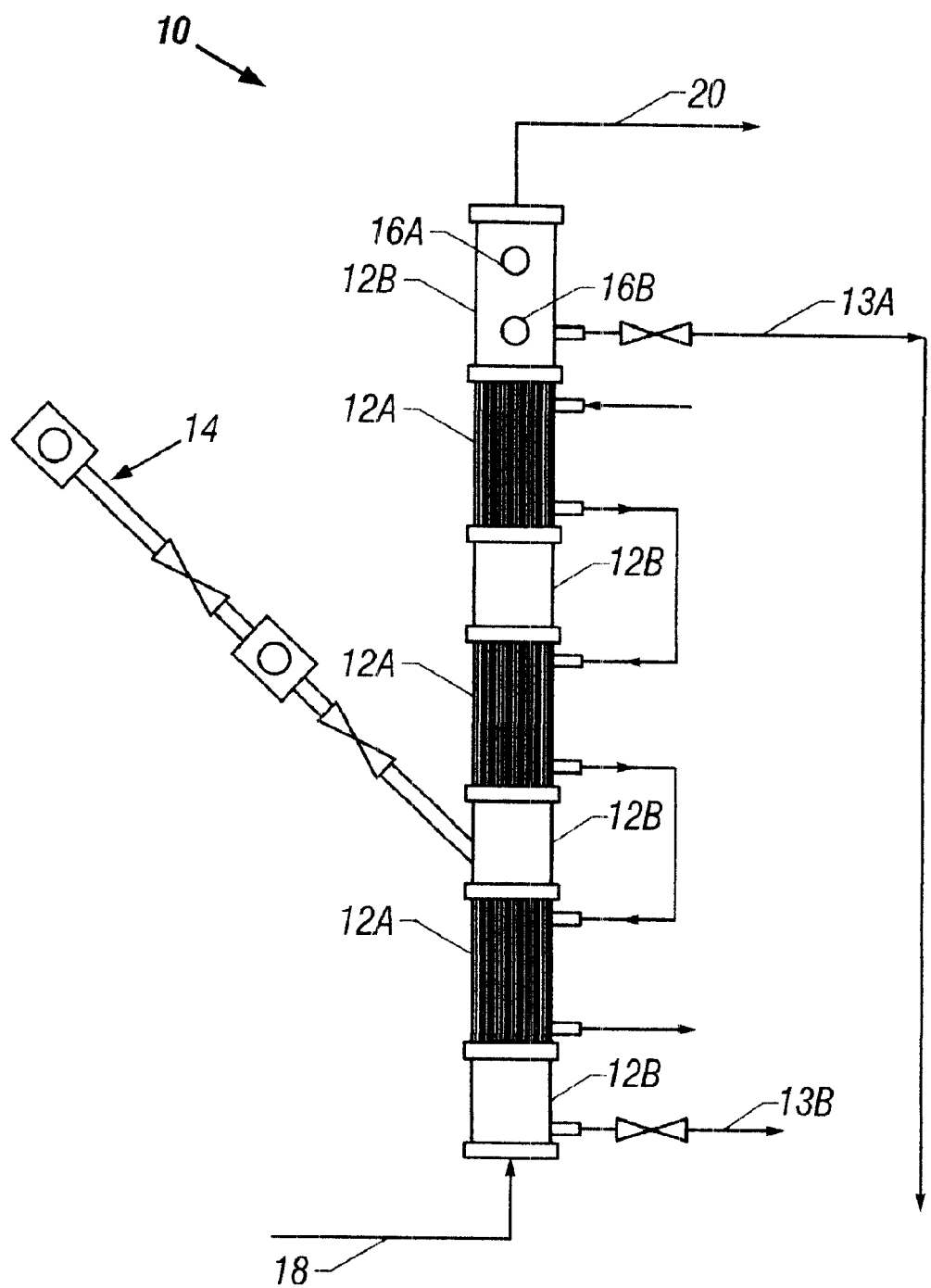
FIG. 1 is a schematic representation of a reactor suitable for use in the present invention.

The present invention relates to a method for carrying out a reaction in the liquid phase using a solid catalyst in powder form to achieve high conversions. In particular, it relates to any application, which has the following characteristics:

Continuous process;

Conversion of reactant(s) approaching that of equilibrium;

Absence of a gas phase (bubbles);

Catalyst is difficult to form into particles of sufficient size to use in a fixed bed; and/or Continuous or semi-continuous feed and withdrawal of catalyst is desired.

In the present invention, a heterogeneous slurry catalyst is mixed with at least one or more liquid hydrocarbon reactants to form a catalyst/reactant mixture. The mixture acts substantially like a fluid which moves up the reactor and allows for ease in recovering both the desired product and the spent catalyst during substantially continuous operation. In essence, the present invention achieves the advantages of using multiple stirred-tanks in series without the need to use multiple tanks.

The present invention provides the method of having the effect of plug flow without the requirement that both reactants be in a liquid phase.

The present invention is useful in connection with any reaction in which a catalyst may be used in a liquid fluidized bed where high conversion is desired. Preferable reactions for use with the present invention include reactions designed to alkylate, hydrogenate, isomerize, and polymerize various compounds.

The invention is suitable for a reaction with one or more reactants. At least one of the reactants must be in the liquid phase and have no separate gas phase It is acceptable if one reactant is a gas, as long as no separate gas bubbles can be detected. With a gas reactant, it is still possible to practice the invention if (a) the gas is dissolved into the liquid reactant phase first or (b) the gas is adsorbed onto the catalyst prior to the catalyst being introduced in the reactor.

The product cannot be gaseous but must be in the liquid phase. Trace impurities may be present in the reactant feed and form gaseous byproducts. The level of trace impurities must be low enough such that only negligible amounts of bubbles are produced by the reaction.

Any heterogeneous catalyst should be suitable for use in the invention as long as it has (1) a particle density higher than the liquid reactants, and (2) a particle size small enough to fluidize upon addition of the liquid reactants. The mean particle size may be less than 1000 microns, preferably less than 500 microns, and most preferably less than 100 microns. Preferred catalysts for use in the present invention are powdered catalysts in which the maximum particle size ratio (largest to smallest) of at least 95% of the particles is less than about 10:1. Examples of such catalysts include alumina, nickel, silica, zeolite, and clay-based catalysts. The height to diameter ratio of the fluid bed must be at least 2:1 to achieve the desired approach to plug flow behavior.

The spent catalyst of the process of this invention may be regenerated. The regenerated catalyst may be fed to the reactor.

Referring now to FIG. 1, in a preferred embodiment, at least some portions of reactor 10 are provided with heat transfer means. Heat transfer in the present invention should be simple because the slurry acts as a liquid. Therefore, an internal coil, a vertical multi-tube bundle, or various external heat exchanger designs may (can) be used to either remove or add heat. A preferred heat exchanger is a vertical multi-tube bundle such as that shown at 12a. This bundle type of heat exchanger is optimum because it is inexpensive, does not plug, and provides a uniform radial temperature profile in the reactor section. Also, it has been found that such bundles have a heat transfer coefficient of >15 BTU/hr-ft$^2$-°F.(78.2 Cal./hr-m$^2$-° C.), which is high enough to control the temperature of most mildly endothermic or exothermic reactions. Conventional techniques for calculating the heat transfer coefficient suggest a much smaller heat transfer coefficient (<3 BTU/hr-ft$^2$-° F.) (14.6 Cal./kg./hr-m$^2$-° C.) because the tube velocities are low (laminar flow). The fact that the actual heat transfer is higher suggests that the heat transfer is enhanced by the presence of the fluidized particles in the reaction medium.

To practice the process of the present invention, a tube 14 is filled with catalyst and liquid reactants are pumped in to form a slurry which is injected into reactor 10. Pilot reactor 10 includes a means to gauge the level of the catalyst slurry. In the pilot reactor 10 shown in FIG. 1, this gauging means may consist of two windows 16a and 16b, one above the other. After the catalyst slurry is injected from tube 14 into reactor 10, the level of the slurry is adjusted to the level of top window 16a. Because the slurry expands when the liquid reactants are added, the slurry is drained, primarily through valve 13a, until the slurry reached the level of lower window 16b, which is about 6" (15.24 cm) below window 16a. The function of lower valve 13b primarily is to remove large catalyst particles that drift to the bottom of the reactor. The means for gauging the level of the slurry may consist of any known slurry level sensor or system.

A slurry is not required for this invention to work. The reactor may be filled with powdered catalyst prior to feeding the liquid hydrocarbon reactant.

Once reactor 10 substantially is filled with slurry from tube 14, the liquid reactants are fed into reactor 10 via line 18. In pilot reactor 10, the liquid reactants may be fed through a porous metal plate to encourage even distribution of the reactants. In a commercial scale reactor, the use of any conventional liquid distributor means would suffice. The liquid reactants preferably are fed into reactor 10 via a line 30 at a velocity such that the liquid reactants will cause "bed lifting," or "fluidization" of the largest particles at 50% of the maximum feed rate. The preferred diameter of the reactor can be calculated using known procedures which depend upon the required velocity of the fluid reactants. See, e.g., R. Perry and D. Green, Perry's Chemical Engineering Handbook, McGraw Hill (6th Ed. 1984), p. 20–59, incorporated herein by reference. The net effect of the liquid reactants rising through the catalyst should be a dense slurry bed which has approximately 50 volume % catalyst and behaves like a liquid.

The invention may be used in connection with any reaction in which the catalyst may be used in a fluidized bed. One nonlimiting example includes the conversion of 5-vinyl-2-norbornene ("VNB") to 5-ethylidene-2-norbornene ("ENB").

With respect to this one embodiment involved in the following examples, the conversion of VNB to ENB is exothermic; therefore, the reaction cannot proceed to a high conversion unless the reaction mixture is cooled at certain intervals. In pilot reactor 10, four non-cooled tube segments 12b optimally were about 4" (10.16 cm) diameter, about 6" (15.24 cm) long, and were interrupted by cooled segments 12a of about 18" (45.72 cm) in length. The optimum tube lengths of 12a and 12b will differ depending upon how exothermic or endothermic a reaction is; however, one of skill in the art should be able to calculate the optimum tube lengths for any particular reaction using known methods which do not require undue experimentation. The height to diameter ratio of the uncooled reactor zone in this embodiment is 6:1.

In order to achieve the beneficial "plug flow" characteristic, it is essential to have sufficient bed height of relatively quiescent catalyst particles with about 50% catalyst as previously described. This is not achieved in the heat transfer zone just described. In fact, the heat transfer zones interrupt the plug flow regime of the reactor and should therefore, be minimized.

Reactor 10 is equipped with an exit line 20 to remove the ENB product once the reaction is complete. A filter is placed in line 20 to remove minor amounts of catalyst particles which are still entrained in the product.

Figure 2:
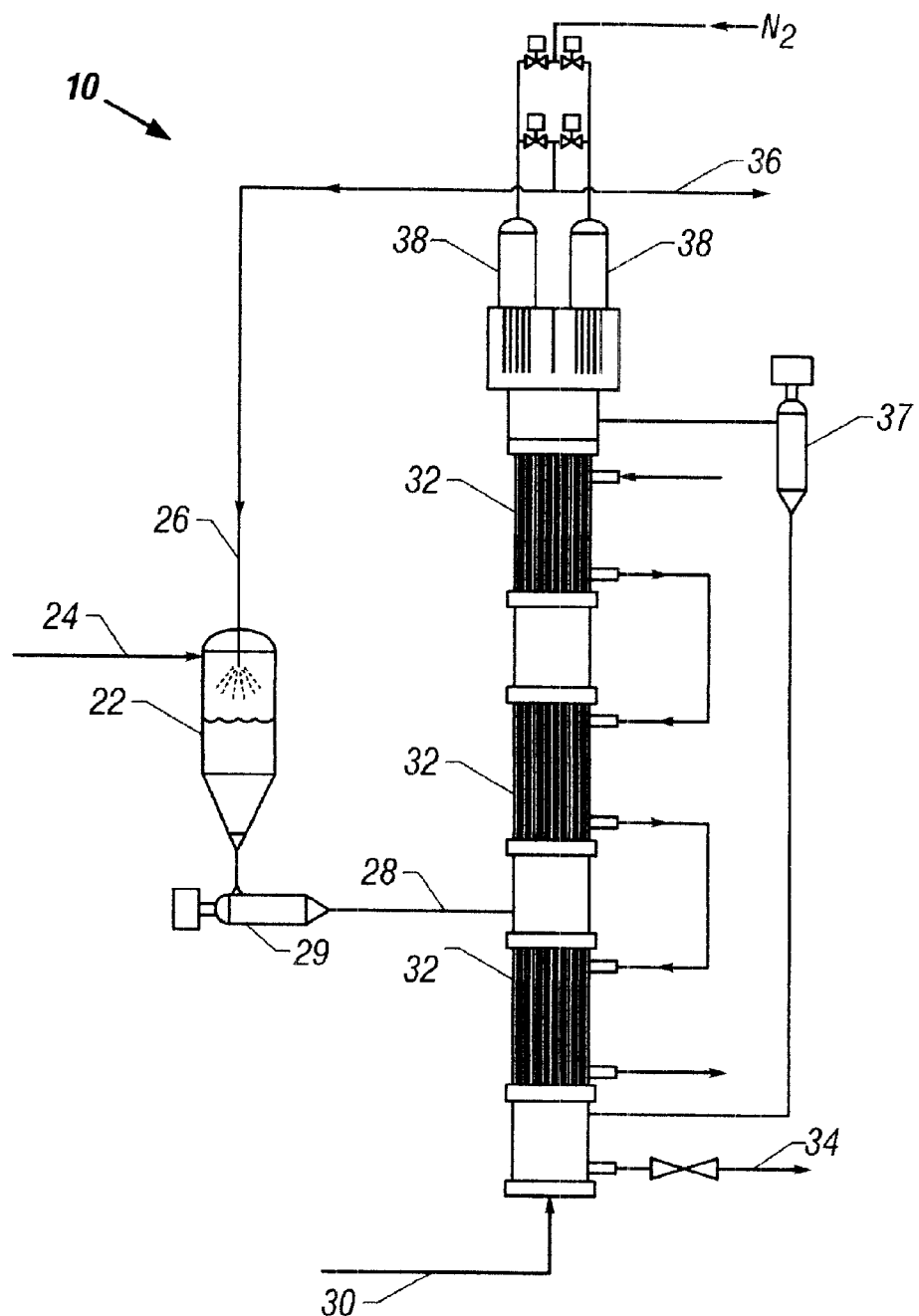
FIG. 2 is a schematic representation of a commercial scale reactor suitable for use in the present invention.

An example of a commercial scale reactor 10 which is suitable for use in the present invention is shown in FIG. 2. Reactor 10 shown in FIG. 2 may be provided with a separate mixer 22 in which the catalyst slurry is prepared. In the depicted embodiment, a catalyst slurry is formed by mixing the catalyst, which is fed to mixer 22 via line 24, with the liquid product, which is fed to mixer 22 via line 26. The catalyst then is injected into reactor 10 via line 28 using a catalyst feed pump 29.

In a preferred embodiment, reactor 10 substantially is filled with catalyst slurry, preferably as detected by slurry level sensors inside reactor 10, before the liquid reactants are added via line 30. Once again, reactor 10 is provided with a heat transfer means 32, and the length of the zones of the reactor which should or should not have such heat transfer means can be determined by the exothermicity or endothermicity of the reaction. Spent catalyst may be removed from reactor 10 via line 34, and the desired product may be removed from reactor 10 via line 36.

Preferably, the reactor is provided with filters 38 through which the liquid product passes before it is removed via line 36. Any conventional solid/liquid separation equipment may be used, including hydrocyclones, which would retain any catalyst fines remaining in the product, and internally and/or externally mounted back-flushable filters, as illustrated at 37 in FIG. 2. It is also helpful for the top of the reactor, above the fluid catalyst level, to be of a larger diameter than the fluid bed section. The lower liquid velocities in this larger diameter section promotes settling of catalyst particles before the product liquid is removed.

One potential problem that might be expected using the present invention would be liquid bypassing and/or back-mixing. Liquid bypassing is minimized in the present invention because the reaction mixture acts like a dense fluid. In laboratory testing, residence time distributions were determined for an 18" (45.72 cm) long×1" (2.54 cm) effective diameter powdered alumina bed. The residence time distributions show that the liquid acted basically like laminar flow.

EXAMPLES

The following examples illustrate both prior art methods and the present invention. Comparative Example A demonstrates that fluidization of a powdered catalyst by a liquid without bubbles is achievable over a range of velocities and bed expansion does exist. Example 1 illustrates the use of this fluidization technique on the high conversion process of isomerizing VNB to ENB on a laboratory scale. Example 2 illustrates the same isomerization process that was conducted in Example 1, but was done on a larger scale to demonstrate operability with heat transfer equipment. Comparative Example 3 demonstrates the negative effect of agitation on the reaction.

Example A

Comparative

Example A demonstrates that fluidization of a powdered catalyst by a liquid without gas bubbles is achievable over a range of velocities. An "armored sight glass" which was 0.53" (1.3462 cm) wide, 1.37" (3.4798 cm) deep, and 18" (45.72 cm) tall was used as the "reactor." The "reactor" was equipped with a porous metal distribution plate on the bottom and filled with 86 grams of powdered alumina, which had an average particle size of 78 microns.

A stream of mixed xylenes, at 27° C., was used as the liquid fluidization medium and flowed through the porous metal distributor into the bottom of the "reactor." The superficial velocity of the fluid was changed by adjusting the feed rate of the mixed xylene stream. The bed height was noted 30 minutes after the velocity was altered. Tests were run using both increasing and decreasing velocities. The bed expansion ratio was calculated by dividing the expanded bed height by the original bed height.

Figure 3:
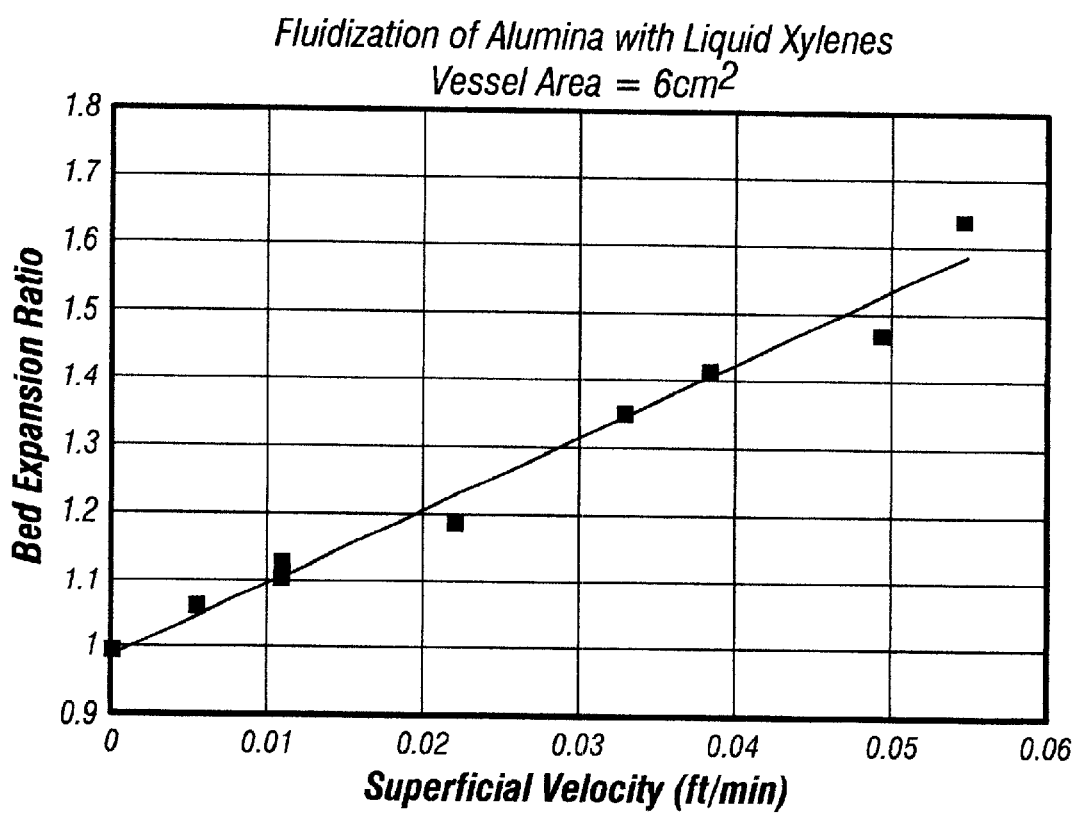
FIG. 3 is a graph of the bed expansion ratio as a function of the superficial fluid velocity from Comparative Example A.

The results of these tests are shown in FIG. 3. This demonstrates that the bed becomes fluidized at a superficial liquid velocity of less than 0.01 ft/sec (0.3048 cm/sec). Catalyst carryover out the top of the reactor was insignificant, and the fluid bed behavior was still evident at a liquid superficial velocity as high as 0.08 ft/sec (2.4384 cm/sec). This illustrates how the bed expands, behaves, and operates.

Example 1

Invention

Example 1 illustrates the use of this fluidization technique on the high conversion process of isomerizing vinyl norbornene (VNB) to ethylidene norbornene (ENB) on a laboratory scale. An alkali metal solid base catalyst was prepared, using the powdered alumina from Example A, and as described in U.S. Pat. No. 3,405,196 (Wolff), which is hereby incorporated by reference for purposes for U.S. practice. The same equipment used in Example A was used in this Example 1.

86 grams of the prepared catalyst were placed in the reactor and the reaction was carried out at atmospheric conditions.

The flow rate of the VNB reactant ranged from 2 ml/min to 10 ml/min, which corresponds to a superficial velocity range of 0.014 ft/min. (0.007112 cm/sec) to 0.070 ft/min. (0.03556 cm/sec). The feed temperature was 80 degrees F (26.67 degrees C), and the effluent temperature was 95 degrees F (35 degrees C). A conversion of 99.8%–99.9% of the equilibrium conversion was achieved. Even though this particular chemical reaction is exothermic and the reaction cannot proceed unless the reaction mixture is cooled at certain intervals, the heat losses through the reactor wall to the air were sufficient to remove the heat of reaction on this small scale, such that heat exchanger equipment was not necessary.

This example illustrates that the fluid bed reactor can approximate plug flow behavior of the reactant(s) as evidenced by the high conversion rates. This would not have been possible in a reactor that was agitated either mechanically or by the use of gas bubbles, as illustrated in Example 3.

Example 2

Invention

Example 2 illustrates the same isomerization process that was conducted in Example 1, but was done on a larger scale to demonstrate operability with heat transfer equipment. The reactor used in this example had the configuration as shown in FIG. 1, consisting of four reactor sections which were separated by three shell and tube type heat exchangers. The heat exchangers were used during the reaction to remove the heat of reaction. The purpose of this test was to prove that it was possible to achieve the desired high conversions using the fluid bed concept in a reactor configuration on a larger scale, using a feed rate of 20 lbs/hr (1514 mls/min) rather than the 2–10 mls/min flowrate, as demonstrated in Example 1.

The heat exchangers of the reactor consisted of four tubes mounted inside of a shell, with the tubes having an internal diameter of 0.9" (2.286 cm) and a length of 18" (45.72 cm). The exchangers were operated such that the isomerization reaction was run on the tube side and the cooling agent, chilled water, was run on the shell side.

The bottom three reactor sections were comprised of 6" (15.24 cm) long segments of 4" (10.16 cm) Schedule 10 stainless steel pipe [4.26" (10.8204 cm) internal diameter] attached to the exchangers and the distributor with flanges. The reactor sections each had a thermocouple inserted three inches from the bottom of the respective section, and the bottom section had a port that allowed the withdrawal of spent catalyst. The second and third sections from the bottom had ports that allowed the addition of air-sensitive catalyst to the reactor. The top reactor section was 18" (45.72 cm) long, and had 2 sets of opposing glass viewing ports that allowed the visual monitoring of catalyst level and surface dynamics.

VNB was fed to the bottom section of the reactor through a porous metal plate distributor that covered the bottom of the reactor.

Catalyst, like that used in Example 1, was added to the reactor until the desired conversion was obtained. At steady state condition, 3500 grams of catalyst were present. After that point, enough catalyst was added to the reactor to make up for losses due to deactivation by poisons in the process feed.

Liquid product was removed from the reactor through a ¼" (0.635 cm) hole in the top flange. VNB was fed at the rate of 20 lbs/hr (544.311 kg/hr) [0.06 ft/min (0.0305 cm/sec) superficial velocity in the reactor sections] of VNB was fed to the bottom of the reactor for 36 hours.

A steady state temperature profile was set up in the reactor, with the reactor sections operating, from the bottom to the top of the reactor, at 12° F. (44.44° C.), 115° F. (46.11° C.), 108° F. (42.22° C.), and 105° F. 40.56° C.). The heat transfer coefficients were measured, and were found to be between 15 and 30 BTU/hr-ft$^2$-° F. (73.2–145 Cal./hr-cm$^2$-° C.) for the heat exchanger sections.

After steady state was achieved, the VNB was converted to ENB at a conversion greater than 99.9% of the equilibrium conversion.

Example 3

Comparative

This example 3 illustrates the effects of having agitation via gas bubbles in the reactor. Example 2 was repeated except that 105 cubic centimeters of nitrogen gas was injected for less than a 1 minute (60 seconds) time period into the catalyst feed part of the bed, which corresponds to the residence time of the bed, resulting in the formation of gas bubbles in the reactor bed zone. The disturbance in the bed resulted in a decrease in conversion from 99.8% to 98.5%.

This example illustrates the importance of minimizing any disturbance to the quiescent liquid fluidized bed in order to achieve the approach to plug flow behavior necessary for reactions where close approach to thermodynamic equilibrium is desired.

We claim:

1. A continuous process for producing 5-ethylidene-2-norbornene (ENB) from a conversion chemical reaction which utilizes a solid catalyst in powdered form comprising:
   a) providing a reactor having a top portion and a bottom portion wherein the length to diameter ratio of the reactor is greater than about 2:1;
   b) loading a powdered heterogeneous catalyst into said reactor;
   c) feeding to said bottom portion of said reactor at least 5-vinyl-2-norbornene (VNB) at a velocity sufficient to disperse said catalyst in said VNB without the use of agitation or back mixing and in the absence of gas bubbles to form a bed reaction zone wherein said velocity is at least equal to the minimum fluidization velocity and less than the minimum entrainment velocity wherein catalyst exits said bed reaction zone in the liquid;
   d) subjecting said VNB to catalyzing conditions in said bed reaction zone whereby said ENB is formed, wherein the conversion rate is higher than 90%; and
   e) removing said ENB from said top portion of said reactor.

2. The process of claim 1, wherein said catalyst and said VNB are continuously replenished.

3. The process of claim 2, wherein said catalyst is fed to said reactor in the form of a slurry comprising at least two components selected from the group consisting of said ENB, said catalyst, and said VNB.

4. The process of claim 1, wherein said catalyst is an alkali metal on alumina.

5. The process of claim 1, wherein said reactor is equipped with means for heat transfer.

6. The process of claim 1, further comprising withdrawing spent catalyst from said reactor.

7. The process of claim 6, wherein said spent catalyst is regenerated.

8. The process of claim 7, wherein said regenerated catalyst is fed to said reactor.

9. The process of claim 1, wherein the conversion rate of the catalytic reaction is higher than 95%.

10. The process of claim 1, wherein the conversion rate of the catalytic reaction is higher than 97%.

11. The process of claim 1, wherein the conversion rate of the catalytic reaction is at least 99.8%.

12. The process of claim 1, wherein the conversion rate of the catalytic reaction is between 90% and 99.9%.

\* \* \* \* \*